United States Patent
LoPinto et al.

[11] Patent Number: 5,916,801
[45] Date of Patent: Jun. 29, 1999

[54] NECTOPHOTOMETER

[76] Inventors: Richard William LoPinto, 88 Willow Ave., Hackensack, N.J. 07601; John Christopher Santelli, 307 Lantana Ave., Englewood, N.J. 07631

[21] Appl. No.: 08/960,529

[22] Filed: Oct. 31, 1997

Related U.S. Application Data

[60] Provisional application No. 60/027,863, Oct. 31, 1996.

[51] Int. Cl.[6] .............................. C12M 1/34; C12Q 1/20
[52] U.S. Cl. ......................... 435/287.1; 435/29; 435/33; 435/288.7; 119/200; 119/267; 356/442; 702/2; 702/19
[58] Field of Search ........................... 435/29, 33, 287.1, 435/288.7, 808, 32; 119/200, 245, 267; 356/440, 442; 436/63; 424/9.2; 702/2, 19; 600/300

[56] References Cited

U.S. PATENT DOCUMENTS

| | | |
|---|---|---|
| 3,951,935 | 4/1976 | Graudums et al. . |
| 3,953,442 | 4/1976 | Demarne . |
| 3,992,265 | 11/1976 | Hansen . |
| 4,077,845 | 3/1978 | Johnson . |
| 4,603,977 | 8/1986 | Bennett et al. . |
| 4,626,992 | 12/1986 | Breaves et al. . |
| 4,723,511 | 2/1988 | Solman et al. . |
| 5,094,944 | 3/1992 | Hayes . |
| 5,569,580 | 10/1996 | Young . |

FOREIGN PATENT DOCUMENTS 33 45 196   7/1985   Germany .

OTHER PUBLICATIONS

Batac–Catalan. Chemical Abstract No. 100:46555 of ASTM Spec. Tech. Publ. (1983), p. 802.
Gabrielyan et al. World Patent Index Abstract No. 82–E3554E of SU 843947 (Jul. 1981).
Schmidt et al.. Chemical Abstract No. 103:208204 of Mycotoxin Res (1985), 1(1), pp. 25–29.

(List continued on next page.)

*Primary Examiner*—William H. Beisner

[57] ABSTRACT

A computer interfaced device for rapidly quantifying levels of toxicity to small aquatic organisms in aqueous environments. The device has a plurality of test chambers containing replicates of a plurality of concentrations of a substance or sample being tested for toxicity. Each chamber also contains a predetermined number of motile aquatic organisms. Light originating on one side of each test chamber is received by a photo-detector on the opposite side. The device's sensitivity is adjusted so that each interruption of a light beam caused by movement of a test organism in each test chamber is recorded for that chamber. Using this device and a toxicity testing protocol both lethality and changes in the frequency of test organism's movement in each concentration of substance or sample is monitored. Toxicity is by convention quantified as the concentration of a substance or sample which causes a predetermined level of lethal or sublethal response usually after a plurality of days. Using simple statistical software, the level of lethality which will occur following a plurality of days of exposure to each concentration can be predicted from motility data generated within just a few hours (usually 2.5 Hours) of exposing test organisms to the substance or sample. The computer includes software responsive to light beam interruption for deriving a set of parameters useful for predicting lethality. The device and accompanying software permits toxicity of a substance or sample to be quantified rapidly from motility data, long before lethality occurs.

3 Claims, 5 Drawing Sheets

OTHER PUBLICATIONS

Diamond, J.M., M. J. Parson, and D. Gruber. Rapid detection of sublethal toxicity using fish ventilatory behavior. *J. Environ. Toc. Chem., 1990* 9:3–11.

Drummone, R.A. and Carlson, R.W. Procedures for measuring cough gill purge rates of fish. EPA 600/3–77–133. (1977) Environmental Protection Agency, Washington DC.

Gruber, D. C.H. Frago and W.J. Rasnake. Automated Biomonitors—first line of defense. *J of Aquatic Ecosystem Health* 1994, 3:87–92.

Gruber, David, J.M. Diamond, M.J. Parson. "Automated Biomonitoring". *Environmental Auditor,* 1991, pp. 229–238, vol. 2, No. 4. . Springer–Verlag New York Inc.

Kramer, K.J.M., H.A. Jenner and D. Zwart. The valve movement response of mussels: A tool in biological monitoring. *Hydrobioloqia* 188/189 (Dev. Hydrobiol, 1989, 54:433–443.

Poels, C.L.M. Continous automatic monitoring of surface water with fish. *Water Treatment Examination* (1975). 24: 46–56.

Sherer, E. and Nowak, S. Apparatus for recording avoidance movement of fish. *J. Fish Res. Board Con.* (1973) 30 1594–1596.

Gruber, D.S. & J.M. Diamond (eds). *Automated biomonitoring: living sensors as environmental montiors.* 1988. pp. 182–205. Ellis Horwood Ltd, Chichester.

Cairns, J. Validating biological monitoring. in: *Automated Biological monitoring: living sensors as environmental monitors,* Gruber, D.S. and J.M. Diamond (eds), (1988) Ellis Horwood Ltd, Chichester.

Cairns, J. Jr., The Genesis of Biomonitoring in Aquatic Ecosystems. *The Environmental Professional: the official journal of the National Association of Environmental Professionals (NAEP),* 1990, pp. 169–176, vol. 12. Pergamon Press.

Cairns, J. and van der Schalie, W.H. Biological Monitoring Part I—Early Warning Systems. (1980) *Wat. Res.* 14, 1179–1196.

Miller, D.C., Lang, W.H., Greaves, J.O.B., R.S. Wilson. *Investigations in aquatic behavioral toxicology using a computerized video quantification system.* (1982) ASTM STP 766. American Society for Testing and Materials, Philadelphia.

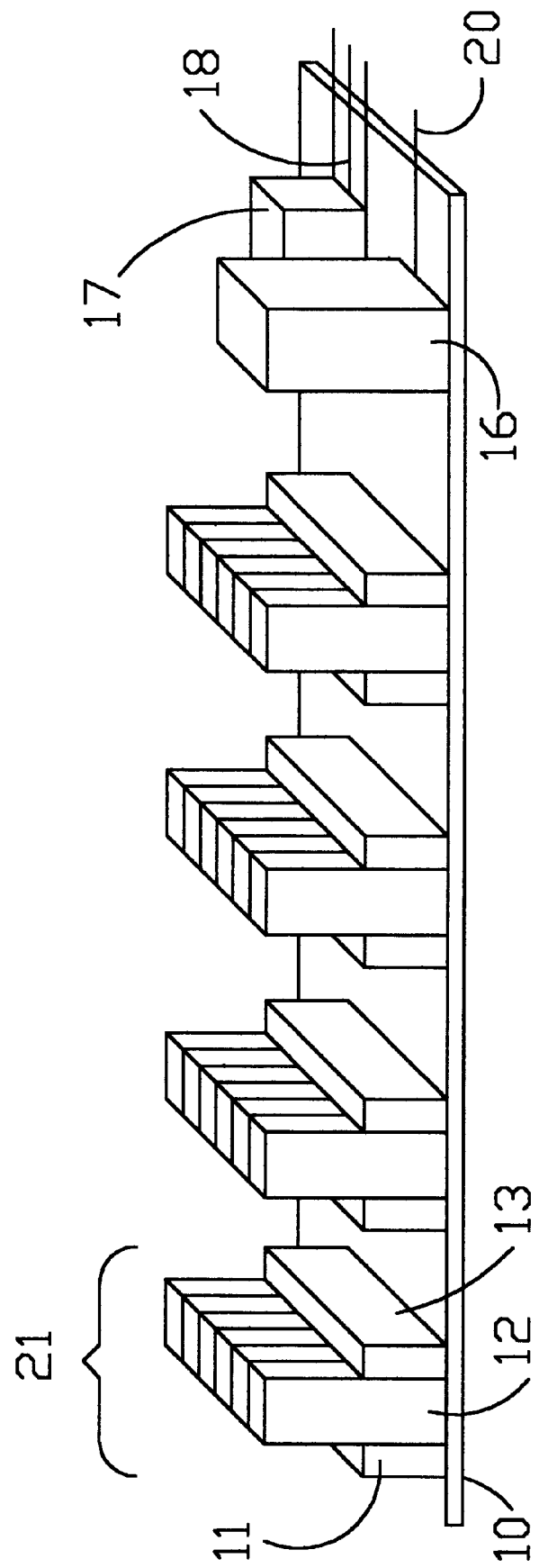

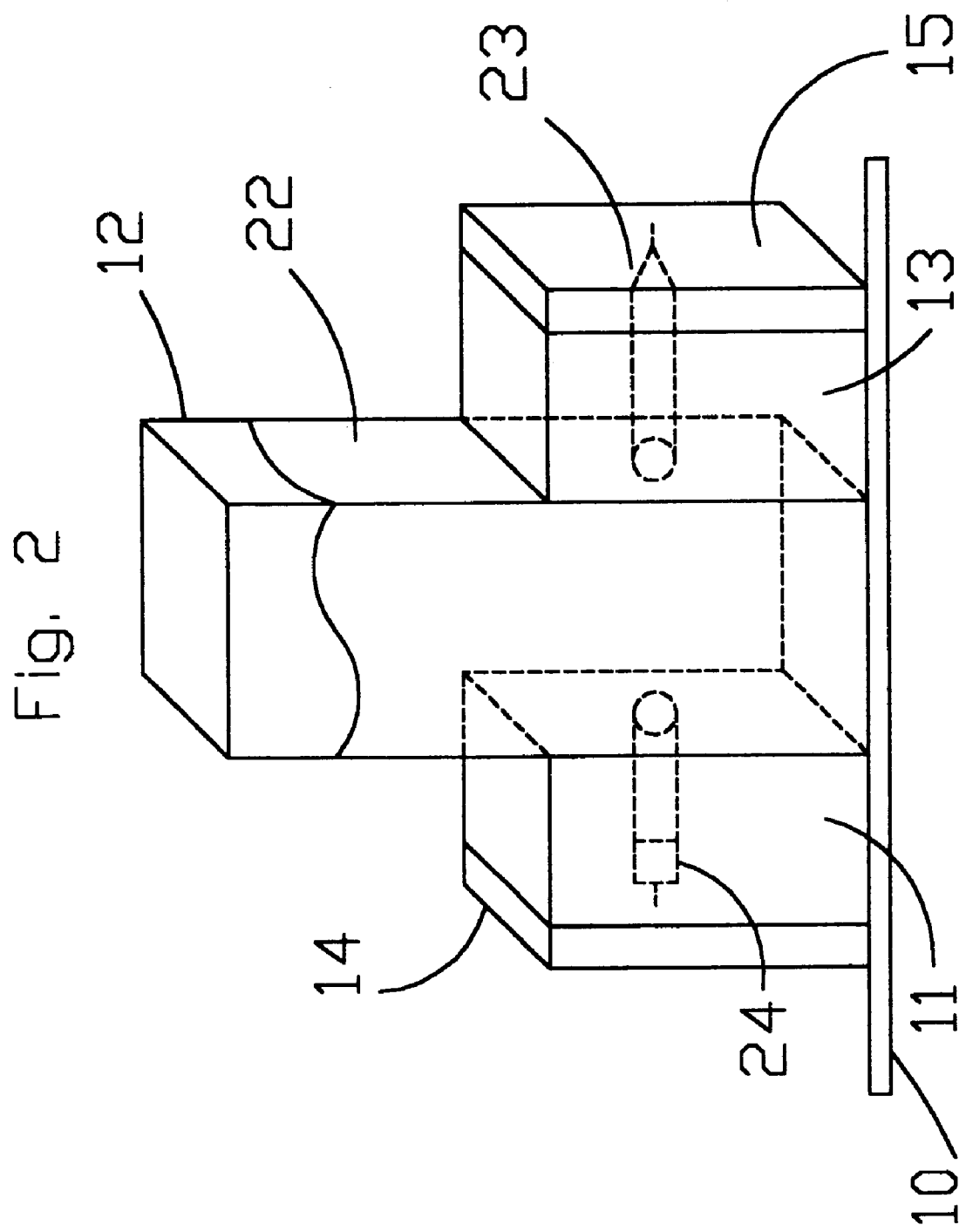

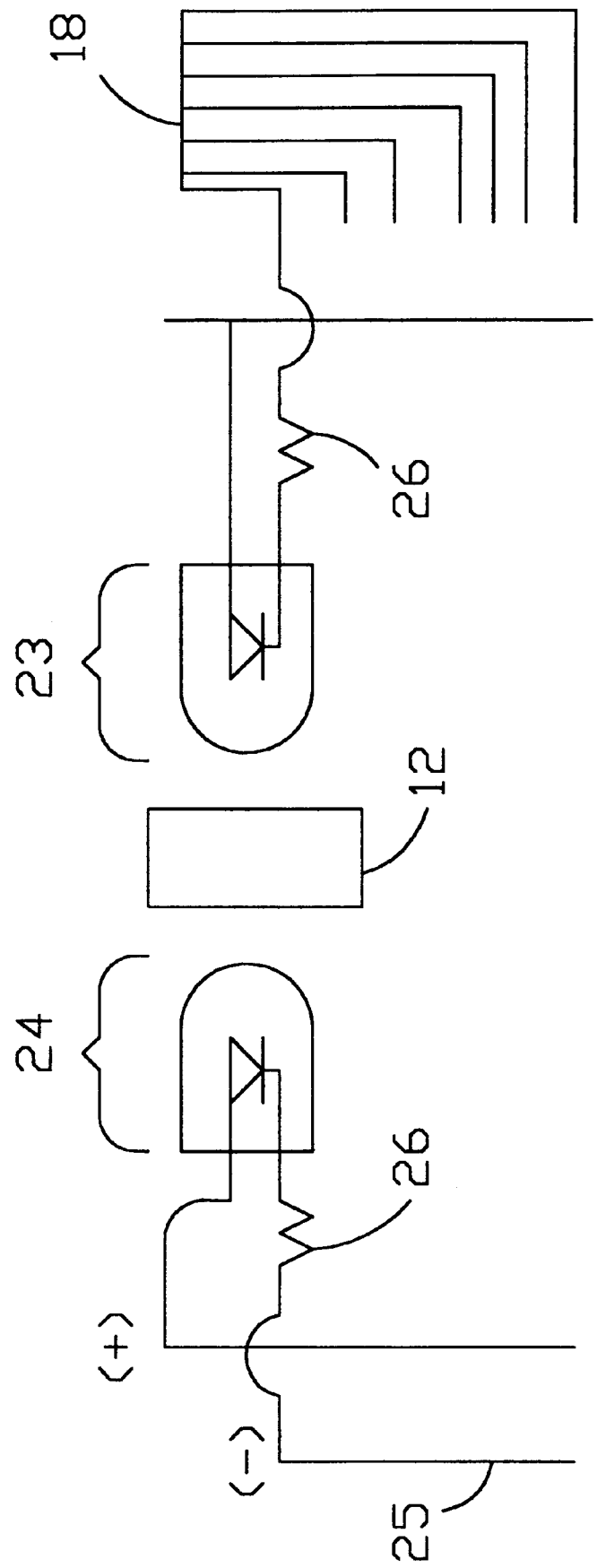

NECTOPHOTOMETER

This application claims the benefit of U.S. Provisional Application Ser. No. 60/027,863, filed Oct. 31, 1996, now abandoned.

BACKGROUND

1. Field of Invention

The present invention relates generally to aquatic environmental toxicology assay systems, and particularly to a device and method which automatically monitors the movements of living organisms exposed to a plurality of concentrations of a substance or sample, and rapidly quantifies the level of toxicity of the substance or sample by analyzing said movements. The present invention also relates to systems for quantifying air quality.

2. Prior Art

Toxicity is defined as a biological effect, specifically it is the concentration of a substance which causes a certain level of adverse effect on living organisms. It is desirable to quantify the toxicity of an effluent or of any material which may enter a water body. Knowing the concentration which is toxic defines the limit for releasing that material to prevent organisms in the water body from an adverse effect. It is also desirable to know if toxic concentrations have been reached in a receiving water. This information helps to identify polluters and it helps dischargers innocent of toxic pollution to escape legal penalties.

Most prior art aquatic environmental toxicology systems, generally termed automated biological monitoring systems (ABMS), are designed to rapidly detect the presence of toxicity in an aqueous environment, especially in water supplies, or in waste-waters and effluents, or receiving waters. The usual purpose of these systems is to provide an early warning of the presence of toxicity. Many of these systems use a computer interfaced device which senses and interprets movement of aquatic organisms to detect toxicity. However, unlike the present invention, these systems can not quantify toxicity because this would require monitoring a plurality of sample concentrations at one time. This is not their purpose and this is not supported by their design. Examples of patents for this type of invention are awarded to John Greaves in 1986, U.S. Pat. No. 4,626,992; and Solman, et.al. (1988), U.S. Pat. No. 4,723,511. The scientific literature describing automated biological monitoring systems (ABMS) designed to rapidly detect the presence of toxicity (but not to quantify it) is also extensive. Some examples are:

Cairns, J. (1988) Validating biological monitoring. in: *Automated Biological monitoring: living sensors as environmental monitors,* Gruber, D. S. and J. M. Diamond (eds), Ellis Horwood Ltd, Chichester]

Cairns, J. Jr., 1990. The Genesis of Biomonitoring in Aquatic Ecosystems. *The Environmental Professional: the official Journal of the National Association of Environmental Professionals (NAEP),* Pergamon Press, vol 12, 1990 p. 169–176.]

Cairns, J. and van der Schalie, W. H. (1980) Biological Monitoring Part I—Early Warning Systems. *Wat. Res.* 14, 1179–1196.

Diamond, J. M., M. J. Parson, and D. Gruber. 1990. Rapid detection of sublethal toxicity using fish ventilatory behavior. *J. Environ. Tox. Chem.* 9:3–11;

Drummond, R. A. and Carlson, R. W. (1977) Procedures for measuring cough gill purge rates of fish. EPA 600/3-77-133. Environmental Protection Agency, Washington, D.C.

Gruber, D. C. H. Frago and W. J. Rasnake. Automated biomonitors—first line of defense. *J of Aquatic Ecosystem Health* 3:87–92, 1994

Gruber, David, J. M. Diamond, M. J. Parson. "Automated Biomonitoring". *Environmental Auditor,* Vol 2, No. 4. pp. 229–238. 1991 Springer-Verlag New York Inc.]

Korver, R. M. and J. B. and Sprague, 1988. A real-time computerized video tracking system to monitor locomotor behavior. In: D. S. Gruber and J. M. Diamond (eds). *Automated biomonitoring: living sensors as environmental monitors.* pp. 182–205. Ellis Horwood Ltd, Chichester Kramer, K. J. M., H. A. Jenner and D. Zwart, 1989. The valve movement response of mussels: A tool in biological monitoring. *Hydrobiologia* 188/189 (Dev. Hydrobiol, 54:433–443.

Miller, D. C., Lang, W. H., Greaves, J. O. B., and Wilson, R. S. (1982). *Investigations in aquatic behavioral toxicology using a computerized video quantification system.* ASTM STP 766. American Society for Testing and Materials, Philadelphia.

Poels, C. L. M. 1975. Continuous automatic monitoring of surface water with fish. *Water Treatment Examination* 24: 46–56.

Sherer, E. and Nowak, S. (1973) Apparatus for recording avoidance movement of fish. *J.Fish Res. Board Con.* 30 1594–1596

Smith, E. H. and H. C. Bailey, 1988. Development of a system for continuous biomonitoring of a domestic water source for early warning of contaminants. In: D. S. Gruber and J. M. Diamond (eds). *Automated biomonitoring: living sensors as environmental monitors.* pp. 182–205. Ellis Horwood Ltd, Chichester There are other prior art aquatic environmental toxicity test systems that do quantify toxicity. They use methods other than motility to indicate a toxic effect. The Microtox system (Azur Environmental Inc.) described by Bulich (ref: Bulich, A. A., 1979. Use of luminescent bacteria for determining toxicity in aquatic environments. In: L. L. Murking and R. A Kimerle (eds). *Aquat. Toxicol.* ASTM STP 667:98–106.) uses a bioluminescent bacterium as a test organism. The fluorescent aquatic bioassay procedure patented by Hayes (1990), U.S. Pat. No. 5,094,944, uses chemically induced fluorescence in a variety of organisms as an indicator of toxicity.

The Microtox system quantifies toxicity by measuring the effect of a toxic liquid on bioluminescence in a particular bacterium. The value of this system is limited because only a particular bacterium may be used for the assay, and the equipment and cost per test is expensive. Because bacterial physiology is significantly different from that of higher organisms the Microtox response to a substance or sample does not necessarily reflect the toxicity response of higher aquatic organisms which may be important living components of aquatic environments. The Microtox system is further limited because the level of toxicity for the test bacterium may be different from that of larger motile aquatic organism which have a completely different physiology. Therefore the Microtox system may not accurately reflect the danger to aquatic organisms and ecosystems which the tested substance may pose.

The fluorescent aquatic bioassay procedure patented by Hayes (1990) requires that the test organism be fed a compound which carries a fluorescent marker. Generally, introducing materials to test organisms, if other than those specifically indicated by a conventional laboratory toxicity test (CLTT) protocol is prohibited by these protocols, and this invalidates the test. This is one reason the US Environmental Protection Agency does not accepted this test as a standard. These materials may interfere with the accuracy of the toxicity test and therefore invalidate the results, and there is a general prohibition against using extraneous chemicals in most US EPA toxicity testing protocols.

OBJECTS AND ADVANTAGES OF THE NECTOPHOTOMETER

There is a clear need in the art for a fast, easy to use bioassay test system that quantifies toxicity without adding extraneous chemicals. The object of the present invention is to provide this type of toxicity test and testing device. In addition the present invention offers, in the same test system and protocol, the advantage two toxicity indicators. These are (1) motility data, which is rapidly generated (usually within three hours); and (2) data on lethality, which is generated over days. In some test protocols (i.e. acute toxicity tests) the latter is the ultimate determinant of toxicity. The advantage of having both types of data generated within one device and one test system is that the two toxicity indicators can be correlated. When a correlation exists as it has in all our tests, the systems accuracy for quantifying toxicity is validated.

Several objects and advantages of my invention are that it may be used for the following purposes:

for performing and for rapidly predicting the results of acute and chronic conventional laboratory toxicity tests (CLTT's) such as those described in the U.S Environmental Protection Agency publication EPA/600/4-90/027F, AUGUST 1993.

for correlating early motility data with the lethality end point of conventional laboratory toxicity test data.

for quantifying behavioral observations made for conventional laboratory toxicity tests. At present these observations made in such tests are subjective, based on the opinion and perspective of a single person observing the organisms. On the other hand, the rate of movement determined with this invention would be a useful objective observation.

for rapidly performing range finding tests. Range finding tests are performed to determine the range of concentrations of liquid which should be used in a conventional laboratory toxicity test. In effect they are a mini-toxicity test which may take a day or more for results to become available. This invention can speed range finding tests and reduce the time needed to get results to a few hours (usually within three hours).

DESCRIPTION OF DRAWINGS

The following figures are provided:

FIG. 1 is a perspective view of our invention

FIG. 2 is a perspective view of one operational unit of the invention

FIG. 3 *b*) is a schematic side view of the invention

FIG. 4 Is a diagram of the led/photo-detector circuit used in the invention

REFERENCE NUMERALS USED IN THE FIGURES

10 BASE
11 SUPPORT WALL WITH LED(S)
12 TEST CHAMBER(S)
13 SUPPORT WALL WITH PHOTO-RECEPTOR(S)
14 JUNCTION BOX WITH CIRCUITRY FOR LED(S)
15 JUNCTION BOX WITH CIRCUITRY FOR PHOTO-DETECTOR(S)
16 SWITCHING POWER SUPPLY
17 50 PIN UNIVERSAL SCREW TERMINATOR
18 CONDUCTOR RIBBON CABLE TO COMPUTER
19 REPLICATES OF OPERATIONAL UNIT GROUPS (REPLICATES OF NO. 21)
20 WIRE TO POWER SOURCE
21 SIX OPERATIONAL UNITS CONSISTING OF ITEMS 11, 12, 13 14, 15
22 LIQUID IN TEST CHAMBER
23 PHOTO-DETECTOR
24 INFRARED LED
25 BUS
26 RESISTOR

SUMMARY

A computer interfaced automated biological monitoring systems monitors and record changes in the motility patterns of aquatic organisms exposed to a plurality of concentrations of substances or examples during toxicity tests. The system uses motility data generated within three hours of exposure to rapidly quantify the toxicity of a substance or sample being tested. The accuracy of this prediction is validated by conventional laboratory toxicity tests. The instrument may be used for the following purposes:

for rapidly quantifying toxicity of a substance or sample in an aquatic environment.

for correlating early motility data with the lethality end point used often for some conventional laboratory toxicity tests.

for rapidly performing range finding tests prior to conventional laboratory toxicity tests thereby speeding the testing process.

for quantifying otherwise subjective assessments about the condition/behavior of organisms upon termination of conventional laboratory toxicity tests.

DESCRIPTION OF THE INVENTION

The invention and its components are shown in several figures as follows:

FIG. 1 is a perspective view of our invention

FIG. 2 is a perspective view of one operational unit of the invention

Figure 3A:
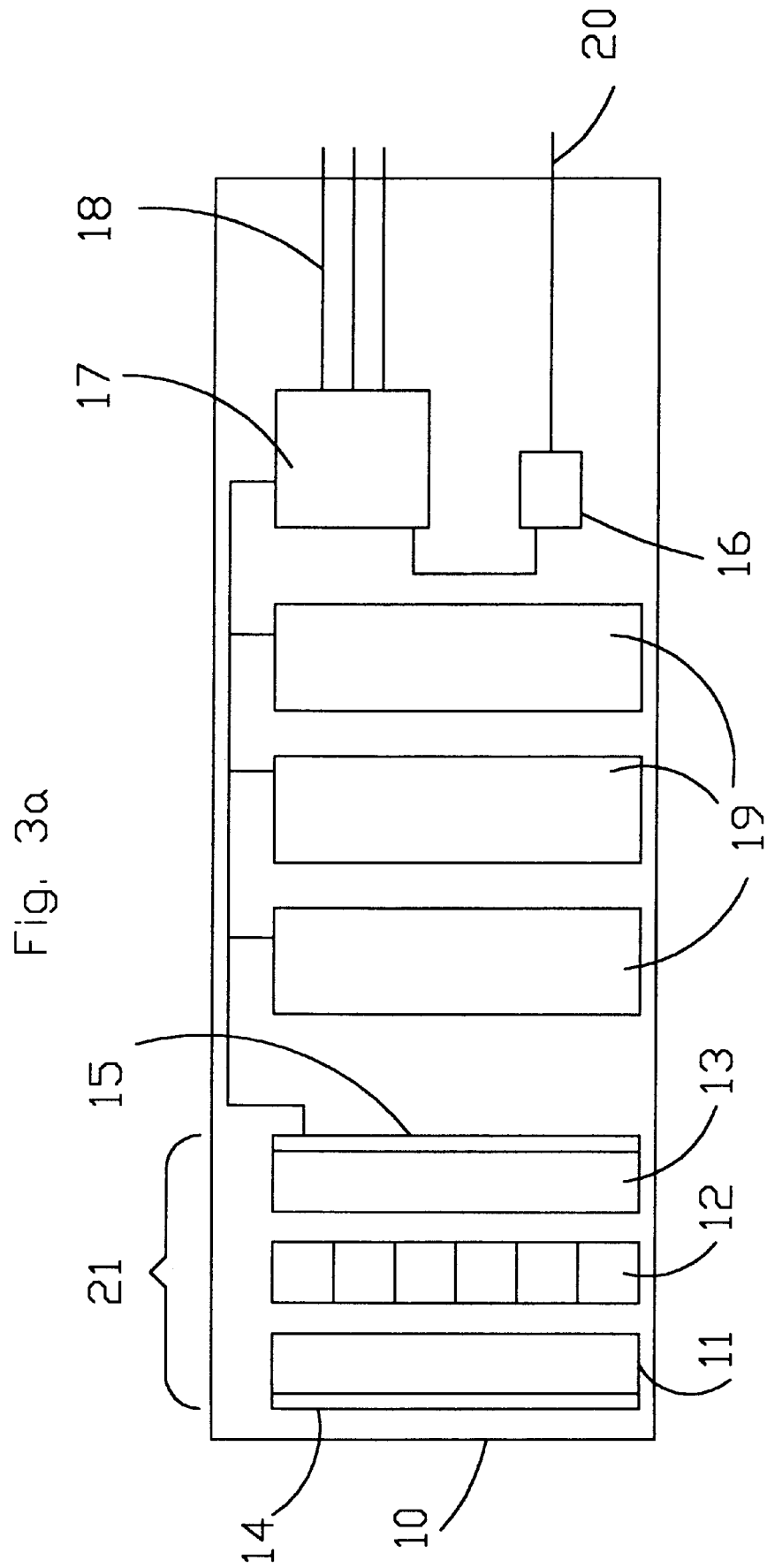
FIG. 3 *a*) is a schematic overhead view of the invention
Figure 3B:
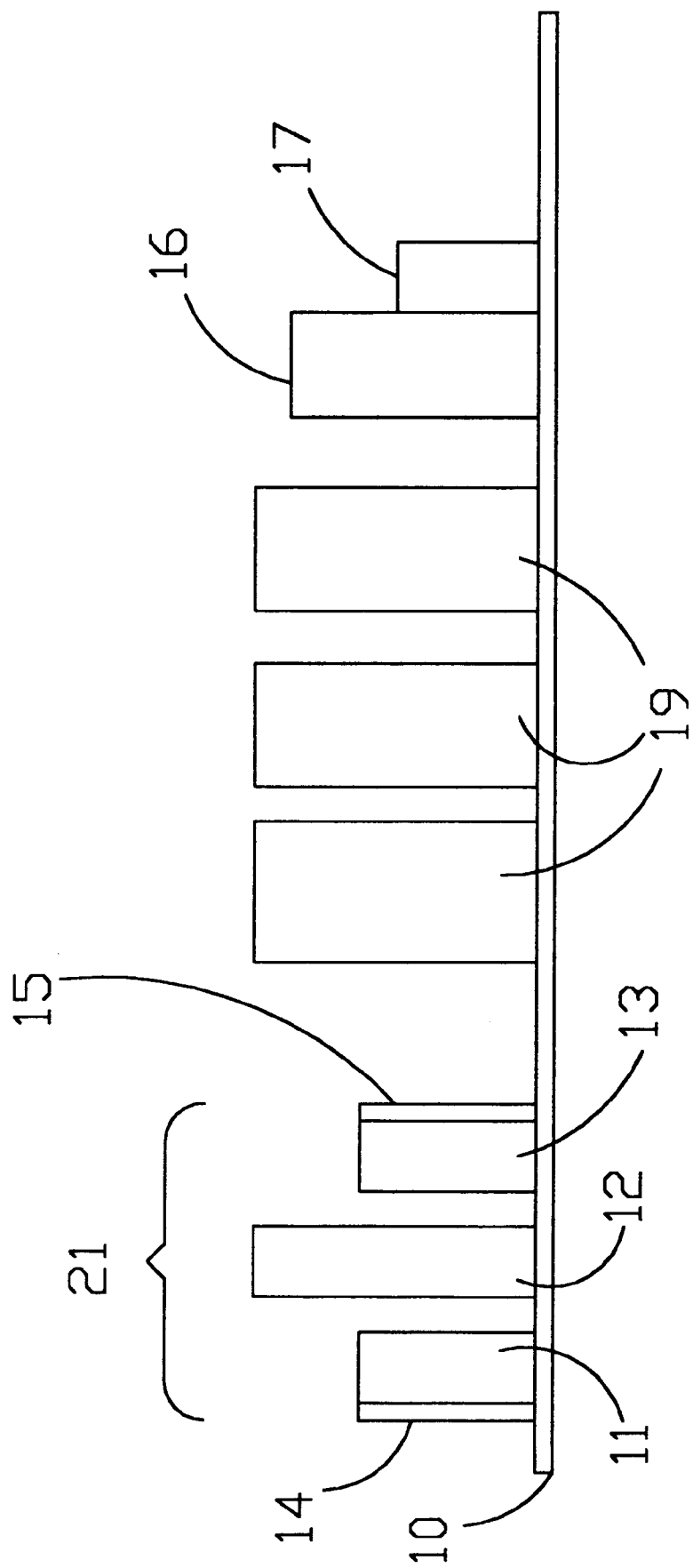

FIG. 3 *a*) is a schematic overhead view of the invention

FIG. 3 *b*) is a schematic side view of the invention

FIG. 4 is a diagram of the LED/photo-detector circuit used in the invention

The instrument which is shown in FIG. 1 can be of any size but has been made as small as 61×21.6×6.35 cm (i.e. 24×8.5×2.5 inches) to facilitate portability. It can operate from an AC or DC power source and has a switching power supply unit 16 which switches power supply from 120 volts AC to 5 volts DC. is seen in (FIGS. 1 and 3A).

The invention consists of a base to which are attached a plurality of operational units 21, shown in FIGS. 1–3 with greatest detail in FIG. 2. Each operational unit consists of a support wall 11 with an infrared LED 24, a test chamber 12, a support wall 13 with a photo-detector 23, a junction box with circuitry for an LED 14, and a junction box with circuitry for a photo-detector 15.

Each member of an LED/photo-detector pair is pressure fitted into holes of approximately 0.32 cm (i.e.⅛ inch) diameter in opposite support walls. The holes between each LED 24 and photo-detector 23 pair are aligned so that only a small, narrow, collimated beam penetrates the test chamber from the LED and to the opposite photo-detector.

On each support wall 11,13 the LED's or the photo-detectors are positioned approximately ⅞ inch from the adjacent unit on that wall. The spacing is such that when the transparent test chambers 12 which are 1×2×7.5 cm in size are inserted one behind the other and fitted snugly between the support walls 11,13, the horizontal center of each of the test chambers is penetrated by a small narrow infrared light beam which then hits a photo-detector 23. For aquatic toxicity tests, test chambers are filled at least to the 5 milliliter level with test solution or with the control aqueous environment. This volume assures that the liquid level is above the light beam and that the light beam will penetrate both the test chambers and the liquid.

The unit is powered by ordinary house hold current which is converted to 5 volt DC. Resistors 26 are arranged so as to make the output of all photo-detectors equivalent for equivalent light input.

OTHER COMPONENTS OF THE INVENTION 386 (or more powerful) computer equipped with:
Universal Driver Software & Manual Programming Language Support
CIO-DAS 48 (48 input digital analogue board), [i.e. 48 SE, 24 DI or 24 4–20 mA A/D Input Brd]

OPERATION

The invention works in conjunction with a 386 computer (or with a more powerful computer), not shown, which has been fitted with a 48 SE, 24 DI or 24 4–20 mA A/D Input Board and which has been appropriately programmed. A copy of the program accompanies this narrative.

Each interruption by a moving organism of the infrared beam that traverses each test chamber is recorded by the computer program as an event. The computer program permits events to be recorded as a function of any unit of time (i.e., an epoch), and the length of the epoch can be set to any convenient length. Therefore the number of events/10 seconds, or per 20 seconds or per 600 seconds etc. can be recorded.

Living Organism Which May Be Used in the Invention

Any organism which normally moves with regularity through a liquid, and which can be accommodated in the test chamber of predetermined size may be used in the instrument. If as is usual movement in test chambers is to be compared then each of the organisms used in a toxicity test must be approximately the same size and the same species. If different sizes or species are used and movement among them is to be compared the instrument must be adjusted to allow each light beam interruption by a single organism to be recorded as an event. (See below: "SETTING THE VOLTAGE BETWEEN THE LED/PHOTORECEPTOR PAIRS")

Other Notes on Equipment or Equipment Adjustments

1. Resistors 26 are arranged so as to make the output of all photo-detectors equivalent for equivalent light input.

2. The computer program written in basic accompanies this narrative.

3. All instructions for operating the instrument appear on the computer when the program is started. Operations are menu driven.

Setting the Voltage Between the Led/Photoreceptor Pairs

Starting the program brings up two columns: "channels" and "data". The "data" for each "channel" (1 channel per chamber) is the voltage produced by the photo-detector as a consequence of the amount of the light reaching it. For each species and size of organism used in the instrument the voltage must be adjusted for maximum sensitivity to light beam disturbance (i.e. interruption) caused by the movement of that organism. If desirable, the instrument can be made sensitive to each size and type of organism by changing photo-detector's resistors or by adjusting the computer program. However, to record events as equivalent when using organisms of the same size and species, the voltage for each of the 24 channels must be approximately the same.

Setting the Upper and Lower Threshold Voltage

The menu then requests that the upper and lower thresholds be set. Generally, the threshold should be 0.3V to 0.5V below the lowest voltage indicated in the data column. For example, when the voltage is 4V, the upper threshold may be set at 3.5V, and the lower threshold may be set at 3.3V.

Setting the Epoch Length

Epochs are the units of time within which disturbances (i.e. events) are recorded for each chamber. Any length of time which suits the test may be chosen. In testing our prototype epoch length was usually set at 600 seconds. For toxicity testing, recording events per selected unit time permits the frequency of movement (i.e. disturbances/unit time) in each liquid sample to be statistically evaluated and correlated with toxicity.

Items Accompanying the Description

TWO COMPUTER PROGRAMS (WRITTEN IN BASIC) FOR OPERATING THE INSTRUMENT
PCTEST.BAS (4 pages)
PCMAIN.BAS (4 pages)

Operating Principle When Used for Testing a Liquid for Toxicity

The instrument assesses toxicity by sensing and recording on computer each movement of organisms/unit time in liquid filled test chambers. Each chamber is penetrated by light from an infrared LED which is then received by a photo-detector. The instrument can be calibrated to be sensitive to the crossing disturbance caused by an organism of a given size and species used in the test. A change in voltage occurs when the light beam is disturbed by the movement of an organism. This is termed an "event". Events per unit time are recorded on computer. The toxicity of the liquid is determined based upon a statistical program which correlates changes in frequency of movement with mortality associated with that frequency.

SUMMARY, RAMIFICATIONS, AND SCOPE

Accordingly the reader will see that this device and method provides a rapid method for quantifying toxicity of a substance or sample. Using this system toxicity is predicted from motility usually in less than three hours. Thus toxicity can be determined much faster than if the test was brought to term and final lethality achieved after a plurality of days as defined in a standard toxicity test protocol. The ability to determine toxicity rapidly, especially of an effluent, may cause a toxic effluent discharger to stop the discharge in time to prevent environmental damage.

We claim:

1. A device for quantifying the toxicity of a substance or sample with respect to test organisms, comprising:
   a plurality of test chambers, each test chamber including a detector means for detecting movement of test organisms within the test chamber;
   a computer electronically linked to each detector means such that movement of the test organisms can be recorded by the computer, said computer including memory which is encoded to:
      record a first set of data which includes movement in each chamber as a function of a predetermined unit of time over a total length of time required to determine mortality of the test organisms in each chamber;
      generate a correlation by using inputted mortality data from the mortality test and said first set of data to statistically correlate changes in frequency of movement with mortality associated with that change in frequency;
      record a second set of data which includes movement in each chamber as a function of said predetermined unit of time over a total length of time which is less than the length of time required to determine mortality;
      predict the toxicity of said substance or sample using said correlation and said second set of data.

2. A method for quantifying the toxicity of a substance or sample with respect to test organisms, comprising:
   providing a plurality of test chambers, each test chamber including a detector means for detecting movement of test organisms within the test chamber;
   providing each test chamber with test organisms and a test substance or sample, wherein each chamber includes a different concentration of said test substance or sample;
   generating a first set of data by recording movement in each chamber as a function of a predetermined unit of time over a total length of time required to determine mortality of the test organisms in each chamber;
   determining mortality of the test organisms in each chamber after said total length of time has elapsed to generate mortality data;
   generating a correlation by using the first set of data and the mortality data to statistically correlate changes in frequency of movement with mortality associated with that change in frequency;
   predicting toxicity of a substance or sample using said correlation and a second set of data which is generated by providing each test chamber with said test organisms and said test substance or sample, wherein each chamber includes a different concentration of said test substance or sample, and recording movement in each chamber as a function of a predetermined unit of time over a total length of time which is less than the length of time required to determine mortality.

3. The method as recited in claim 2, wherein said second set of data is used to determine the range of concentrations of substance or sample which is appropriate to use in a conventional laboratory toxicity test.

* * * * *